US011414653B2

(12) United States Patent
Gladden et al.

(10) Patent No.: US 11,414,653 B2
(45) Date of Patent: Aug. 16, 2022

(54) **PROMOTER USEFUL FOR HIGH EXPRESSION OF A HETEROLOGOUS GENE OF INTEREST IN *ASPERGILLUS NIGER***

(71) Applicants: The Regents of the University of California, Oakland, CA (US); National Technology & Engineering Solutions of Sandia, LLC, Albuquerque, NM (US); Pacific Northwest National Laboratory (PNNL), Richland, WA (US)

(72) Inventors: John M. Gladden, Alameda, CA (US); Saori Amaike Campen, San Diego, CA (US); Jinxiang Zhang, Albany, CA (US); Jon K. Magnuson, Richland, WA (US); Scott E. Baker, Richland, WA (US); Blake A. Simmons, San Francisco, CA (US)

(73) Assignees: National Technology & Engineering Solutions of Sandia, LLC, Albuquerque, NM (US); Battelle Memorial Institute, Richland, WA (US); The Regents of the University of California, Oakland, CA (US)

( * ) Notice: Subject to any disclaimer, the term of this patent is extended or adjusted under 35 U.S.C. 154(b) by 874 days.

(21) Appl. No.: 16/124,127

(22) Filed: Sep. 6, 2018

(65) Prior Publication Data
US 2019/0169584 A1 Jun. 6, 2019

Related U.S. Application Data

(60) Provisional application No. 62/554,743, filed on Sep. 6, 2017.

(51) Int. Cl.
| C12N 15/80 | (2006.01) |
| C07K 14/38 | (2006.01) |
| C12N 9/30 | (2006.01) |
| C12N 9/42 | (2006.01) |

(52) U.S. Cl.
CPC .............. *C12N 9/242* (2013.01); *C07K 14/38* (2013.01); *C12N 9/2445* (2013.01); *C12N 15/80* (2013.01); *C12Y 302/0102* (2013.01); *C12Y 302/01021* (2013.01)

(58) Field of Classification Search
None
See application file for complete search history.

(56) References Cited

PUBLICATIONS

Andersen et al. Comparative genomics of citric-acid-producing Aspergillus niger ATCC 1015 versus enzyme-producing CBS 513. 88. 2011. Genome Research. vol. 21, p. 885-897. (Year: 2011).*

McCutcheon et al. Characterization of a heat resistant beta-glucosidase as a new reporter in cells and mice. 2010. BMC Biology. vol. 8, No. 89, p. 1-8. (Year: 2010).*
Takada et al. The Cell Surface Protein Gene ecm33+ is a Target of the Two Transcription Factors Atf1 and Mbx1 and Negatively Regulates Pmk1 MAPKCell Integrity Signaling in Fission Yeast. Feb. 15, 2010. Molecular Biology. vol. 21, p. 674-685. (Year: 2010).*
Fang et al. E3 Ubiquitin Ligase Pub1 is implicated in Endocytosis of a GPI-Anchored Protein Ecm33 in Fission Yeast. 2014 Plos One 9(1), 1-11 (Year: 2014).*
Klein-Marcuschamer et al., "The challenge of enzyme cost in the production of lignocellulosic biofuels." Biotechnol Bioeng 109:1083-1087 (2012).
Naik et al., "Production of first and second generation biofuels: A comprehensive review." Renew Sustain Energy Rev. 14:578-597 (2010).
Liu et al., "Cost evaluation of cellulase enzyme for industrial-scale cellulosic ethanol production based on rigorous Aspen Plus modeling." Bioprocess Biosyst Eng. 39:133-140 (2016).
D'haeseleer et al., "Proteogenomic Analysis of a Thermophilic Bacterial Consortium Adapted to Deconstruct Switchgrass." PLoS One 8, e68465 (2013), 11 pages.
Gladden et al, "Discovery and characterization of ionic liquid-tolerant thermophilic cellulases from a switchgrass-adapted microbial community." Biotechnol Biofuels 7:15 (2014), 12 pages.
Schuster et al., "On the safety of Aspergillus niger—A review." Appl Microbiol Biotechnol 59:426-435 (2002).
Sewalt et al., "The Generally Recognized as Safe (GRAS) Process for Industrial Microbial Enzymes." Ind Biotechnol 12:295-302 (2016).
Punt et al., "Filamentous fungi as cell factories for heterologous protein production." Trends Biotechnol, p. 200-206 (2002).
Pel et al., "Genome sequencing and analysis of the versatile cell factory Aspergillus niger CBS 513.88." Nat Biotechnol 25:221-231 (2007).
Andersen et al., "Comparative genomics of citric-acid-producing Aspergillus niger ATCC 1015 versus enzyme-producing CBS 513. 88." Genome Res 21:885-897 (2011).
Baker et al., "Aspergillus niger genomics: past, present and into the future." Med Mycol 44 Suppl 1:S17-21 (2006).
Park et al., "A thermophilic ionic liquid-tolerant cellulase cocktail for the production of cellulosic biofuels." PLoS One, 7, E37010 (2012).
Amaike Campen et al., "Expression of naturally ionic liquid-tolerant thermophilic cellulases in Aspergillus niger." PLoS One 12 (2017), 15 pages.
Fowler et al., "Regulation of the glaA gene of Aspergillus niger." Curr Genet 18:537-545 (1990).
Petersen et al, "A new transcriptional activator for amylase genes in Aspergillus." Mol Gen Genet 262:668-676 (1999).

(Continued)

*Primary Examiner* — Nancy J Leith
*Assistant Examiner* — Tiffany Nicole Grooms
(74) *Attorney, Agent, or Firm* — Robin C. Chiang; Lawrence Berkeley National Laboratory

(57) ABSTRACT

The present invention provides for an *Aspergillus niger* host cell comprising a gene of interest operatively linked to an ecm33 promoter of an ascomycete fungi, wherein the gene of interest is heterologous to the ecm33 promoter and/or to *Aspergillus niger*. In some embodiments, the gene of interest is a glycoside hydrolase enzyme. In some embodiments, the glycoside hydrolase enzyme is a glucosidase.

12 Claims, 5 Drawing Sheets

Specification includes a Sequence Listing.

(56) References Cited

PUBLICATIONS

Gouka et al., "An expression system based on the promoter region of the Aspergillus awamori 1,4-beta-endoxylanase A gene." Appl Microbiol Biotechnol 46:28-35 (1996).
Punt et al., "Functional elements in the promoter region of the Aspergillus nidulans gpdA gene encoding glyceraldehyde-3-phosphate dehydrogenase." Gene 93:101-109 (1990).
Punt et al., "An upstream activating sequence from the Aspergillus nidulans gpdA gene." Gene 120:67-73 (1992).
Ferreira et al., "Proteomic analysis of the secretory response of Aspergillus niger to D-maltose and D-xylose." PLoS One 6 (2011).
Minetoki et al., "Improvement of promoter activity by the introduction of multiple copies of the conserved region III sequence, involved in the efficient expression of Aspergillus oryzae amylase-encoding genes." Appl Microbiol Biotechnol, 50:459-467 (1998).
Chiang et al., "Characterization of a polyketide synthase in Aspergillus niger whose product is a precursor for both dihydroxynaphthalene (DHN) melanin and naphtho-y-pyrone" Fungal Genet Biol 48:430-437 (2011).
Punt et al., "Transformation of Aspergillus based on the hygromycin B resistance marker from *Escherichia coli*." Gene 56:117-124 (1987).
Lubertozzi et al.,"Developing Aspergillus as a host for heterologous expression". Biotechnol Adv, 27: 53-75 (2009).
Kitano et al., "Specific expression and temperature-dependent expression of the acid protease-encoding gene (pepA) in Aspergillus oryzae in solid-state culture (rice-koji)." J Biosci Bioeng 93:563-567 (2002).
Kulmburg et al., "Specific binding sites in the alcR and alcA promoters of the ethanol regulon for the CREA repressor mediating carbon cataboiite repression in Aspergillus nidulans." Mol Microbiol 7:847-857 (1993).
Qiu et al., "Detection of a protein, AngCP, which binds specifically to the three upstream regions of glaA gene in A. niger T21." Sci China C Life Sci 45:527-537 (2002).
Aro et al., "ACEI of Trichoderma reesei is a repressor of cellulase and xylanase expression." Appl Environ Microbiol 69:56-65 (2003).
Saloheimo et al., "Isolation of the ace1 gene encoding a Cys2-His2 transcription factor involved in regulation of activity of the cellulase promoter cbh1 of Trichoderma reesei." J Biol Chem 275:5817-5825 (2000).
Takada et al., The cell surface protein gene ecm33+ is a target of the two transcription factors Atf1 and Mbx1 and negatively regulates Pmk1 MAPK cell integrity signaling in fission yeast. Mol Biol Cell 21:674-685 (2010).
Ouyang et al., "One single basic amino acid at the ω-1 or ω-2 site is a signal that retains glycosylphosphatidylinositol-anchored protein in the plasma membrane of Aspergillus fumigatus." Eukaryot Cell 12:889-99 (2013).
Zhang et al., "Disruption of the cell wall integrity gene ECM33 results in improved fermentation by wine yeast." Metab Eng 45:255-264 (2018).
Gil-Bona et al., Global Proteomic Profiling of the Secretome of Candida albicans ecm33 Cell Wall Mutant Reveals the Involvement of Ecm33 in Sap2 Secretion. J Proteome Res 14:4270-4281 (2015).
Champer et al., "Proteomic Analysis of Pathogenic Fungi Reveals Highly Expressed Conserved Cell Wall Proteins." J fungi 2:6 (2016), 19 pages.
Yin et al., "Comparative genomics and transcriptome analysis of Aspergillus niger and metabolic engineering for citrate production." Sci Rep 7:41040 (2017),16 pages.
Gil-Bona et al., "The cell wall protein Ecm33 of Candida albicans is involved in chronological life span, morphogenesis, cell wall regeneration, stress tolerance, and host-cell interaction." Front Microbiol 7 (2016) 14 pages.
Martinez-Lopez et al., "The GPI-anchored protein CaEcm33p is required for cell wall integrity, morphogenesis and virulence in Candida albicans." Microbiology 150:3341-3354 (2004).
Romano et al., "Disruption of the Aspergillus fumigatus ECM33 homologue results in rapid conidial germination, antifungal resistance and hypervirulence." Microbiology 152:1919-1928 (2006).
Pardo et al., "PST1 and ECM33 encode two yeast cell surface GPI proteins important for cell wall integrity." Microbiology 150:4157-4170 (2004).
Koda et al., "5' untranslated region of the Hsp12 gene contributes to efficient translation in Aspergillus oryzae." Appl Microbiol Biotechnol, 70:333-336 (2006).
Koda et al., "Translation efficiency mediated by the 5' untranslated region greatly affects protein production in Aspergillus oryzae." Appl Microbiol Biotechnol, 66:291-296 (2004).
Szewczyk et al., "Fusion PCR and gene targeting in Aspergillus nidulans." Nat Protoc 1:3111-3120 (2006).
Colot et al., "A high-throughput gene knockout procedure for Neurospora reveals functions for multiple transcription factors." Proc Natl Acad Sci U S A 103:10352-10357 (2006).
Yelton et al., "Transformation of Aspergillus nidulans by using a trpC plasmid." Proc Natl Acad Sci U S A 81:1470-1474 (1984).
Ward et al., "Characterization of humanized antibodies secreted by Aspergillus niger." Appl Environ Microbiol 70:2567-2576 (2004).
Livak et al., "Analysis of relative gene expression data using real-time quantitative PCR and the 2(-Delta Delta C(T)) Method." Methods 25:402-408 (2001).
Bok et al., "Fast and easy method for construction of plasmid vectors using modified quick-change mutagenesis." Methods Mol Biol 944:163-74 (2012).
Su et al., "Heterologous Gene Expression in Filamentous Fungi." Adv Appl Microbiol 81:1-61 (2012).

\* cited by examiner

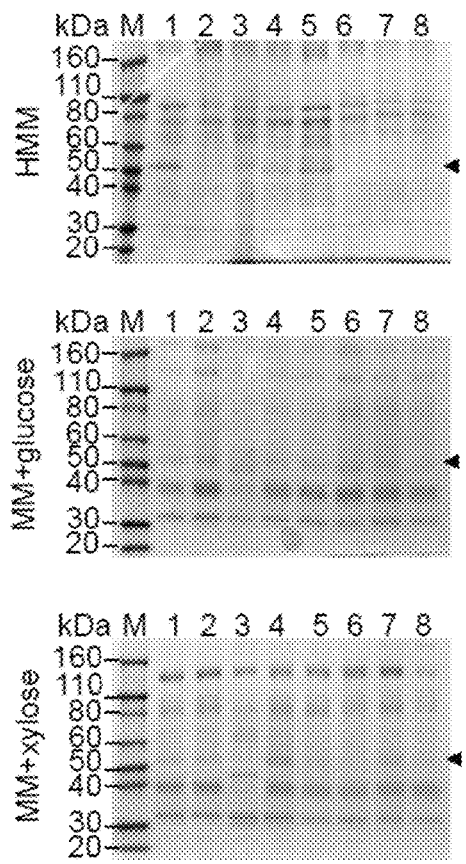
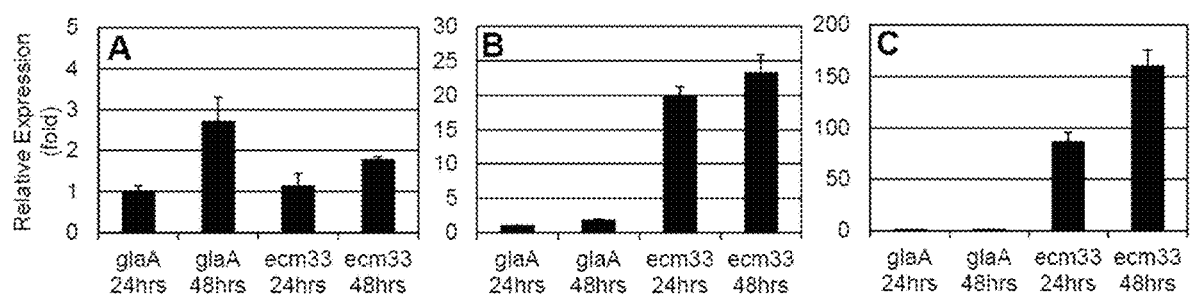
FIG. 4
FIG. 5

PROMOTER USEFUL FOR HIGH EXPRESSION OF A HETEROLOGOUS GENE OF INTEREST IN *ASPERGILLUS NIGER*

RELATED PATENT APPLICATIONS

The application claims priority to U.S. Provisional Patent Application Ser. No. 62/554,743, filed Sep. 6, 2017, which is herein incorporated by reference in its entirety.

STATEMENT OF GOVERNMENTAL SUPPORT

The invention was made with government support under Contract Nos. DE-AC02-05CH11231 awarded by the U.S. Department of Energy. The government has certain rights in the invention.

FIELD OF THE INVENTION

The present invention is in the field of enzyme expression in *Aspergillus niger*.

SEQUENCE LISTING

The instant application contains a Sequence Listing which has been submitted electronically in ASCII format and is hereby incorporated by reference in its entirety. Said ASCII copy, created on Feb. 19, 2019, is named 2016_092_02_Sequence_Listing_TT25.txt and is 6470 bytes in size.

BACKGROUND OF THE INVENTION

Efficient and economical deconstruction of biomass is critical for the success of lignocellulosic biorefineries. Biomass pretreatment with ionic liquids (ILs) tackles this issue as it increases biomass saccharification efficiency at lower cellulose loadings. However, some ILs inhibit the activity of commercial cellulases and must be first be removed from the biomass, which is a costly mitigation. Ascomycete fungus, *Aspergillus niger*, has been widely used for high titer enzyme production.

Deconstruction of lignocellulosic biomass is one of the challenges to develop lignocellulolytic biofuel which have a great potential to reduce petroleum-based fuel dependency. Pretreatment of the biomass with ionic liquid (IL) helps to subsequent enzymatic hydrolysis to sugar. These glycoside hydrolases are the major cost drivers of the deconstruction process, and therefore development of technologies that reduce enzyme costs will be critical for the successful commercialization of lignocellulosic biofuels (1-3). In previous studies, thirty-seven cellulases derived from a thermophilic biomass-adapted microbial community were identified and isolated for optimization of saccharification with high temperature in the presence of ionic liquid (IL), which was great promise for lignocellulolytic enzymatic hydrolysis (4, 5). Twenty-one of these enzymes were expressed in *E. coli* and eighteen of these enzymes were active with at least 10% of IL presence (5). These results supported thermophilic and IL-tolerant cellulase cocktail for lignocellulolytic hydrolysis, however, the amount of enzyme production needed to improve at high titer level with these thermophilic and IL-tolerant function. To increase the production amount, we utilized the filamentous fungi for the basal heterologous expression system.

*Aspergillus niger* is a filamentous fungus in ascomycete and naturally capable to secrete a wide range of enzymes for pharmaceutical and food industries. The fungus is a generally regarded as safe organism (GRAS) approved by the U.S. Food and Drug Administration (FDA)(6, 7) for the consumptions of human and animal food enzyme and have been utilized as a resourceful cell factory for various purposes (8). At least 10 different strains of *A. niger* have been genome sequenced, including industrial-enzyme producing strain, CBS513.88 (9) and citric acid producing strain, ATCC1015 (10). The strain ATCC11414 (NRRL2270) of *A. niger* is derived from genome-sequenced strain, ATCC1015 with improving the capability of citric acid production (11). Previously, we randomly integrated a total of 32 thermophilic IL-tolerant bacterial and known fungal cellulases into *A. niger* expression system in ATCC11414 strain and evaluated their enzyme production. One of the beta-glucosidases, A5IL97 (UniProt ID)(12), isolated from *Thermotoga petrophila* showed the highest activity and further compared in bacterial and fungal heterologous expression system. These results suggest that *A. niger* is a good expression host for heterologous cellulase and the fungus is capable to produce more commercially relevant titers of these enzymes with genetic engineering (13). There are well-established molecular biological tools available for the fungus. Several promoters have been identified and applied to native or heterologous enzyme production in *A. niger*, such as glucoamylase (glaA) promoter (14), amylase (amyR) promoter (15), endoxylanaese (exlA) promoter (16) and strong constitutive glyceraldehyde-3-phosphate hydrogenase (gpdA) promoter (17, 18).

SUMMARY OF THE INVENTION

The present invention provides for an *Aspergillus niger* host cell comprising a gene of interest operatively linked to an ecm33 promoter of an ascomycete fungi, wherein the gene of interest is heterologous to the ecm33 promoter and/or to *Aspergillus niger*.

The present invention provides for a nucleic acid encoding a gene of interest operatively linked to an ecm33 promoter of an ascomycete fungi, wherein the gene of interest is heterologous to *Aspergillus niger*.

The present invention provides for a vector comprising the nucleic acid of the present invention. In some embodiments, the vector is an expression vector.

The present invention provides for an *Aspergillus niger* host cell comprising the nucleic acid of the present invention.

The present invention provides for a method of expressing a heterologous gene of interest in an *Aspergillus niger* host cell, comprising: (a) optionally constructing the nucleic acid of the present invention, (b) introducing the nucleic acid into an *Aspergillus niger* host cell, (c) culturing or growing the host cell in a medium suitable for expressing the gene of interest, and (d) optionally separating or purifying the gene product encoded by the gene of interest from the rest of the host cell and/or medium.

In some embodiments, the gene of interest is a glycoside hydrolase enzyme. In some embodiments, the glycoside hydrolase enzyme is a glucosidase.

BRIEF DESCRIPTION OF THE DRAWINGS

The foregoing aspects and others will be readily appreciated by the skilled artisan from the following description of illustrative embodiments when read in conjunction with the accompanying drawings.

FIG. 4. SDS-PAGE of A5IL97 secretion in promoter mutants. Each incubated culture under three different media conditions were collected, concentrated, and loaded 10 ul of each to Tris-Glycine SDS-PAGE gel with 1× Tris-Glycine Running Buffer, following staining with Coomassie blue. Each lane represented M: marker, 1: glaA promoter mutant, 2: pepA promoter mutant, 3: ecm33 promoter mutant, 4: gpdA promoter mutant, 5: rnt2 promoter mutant, 6: agdA promoter mutant, 7: ast1 promoter mutant, and 8: sed2 promoter mutant. Black arrows indicated the expected A5IL97 protein size.

FIG. 5. A5IL97 mRNA gene expression. Relative A5IL97 gene expression with glaA promoter and ecm33 promoter mutants were measured by qRT-PCR and normalized to glaA promoter at each 24-hour sample under three different media conditions; Panel A: HMM media, Panel B: MM plus glucose, Panel C: MM plus xylose. Error bars showed the standard deviations of three replications.

DETAILED DESCRIPTION OF THE INVENTION

Figure 1:
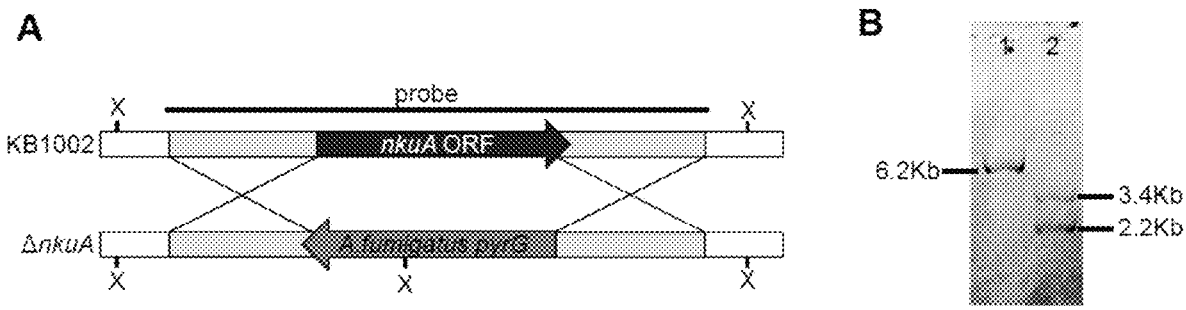
FIG. 1. Diagram and Southern blot of nkuA ORF deletion in *A. niger*. Panel A. Diagram of *A. niger* pyrG– strain, KB1002 ORF nkuA replacement with *A. fumigatus* pyrG–. Mutants were confirmed by Southern blot using approximately 4.5 kb of the probe and two different restriction enzymes, XhoI (X) and EcoNI (not shown). Panel B. Southern blot. The XhoI digestion showed a 6.2 kb fragment in wild type (Lane 1) and 2.2 and 3.4 kb fragments in ΔnkuA strain (Lane 2).

Before the invention is described in detail, it is to be understood that, unless otherwise indicated, this invention is not limited to particular sequences, expression vectors, enzymes, host microorganisms, or processes, as such may vary. It is also to be understood that the terminology used herein is for purposes of describing particular embodiments only, and is not intended to be limiting.

In this specification and in the claims that follow, reference will be made to a number of terms that shall be defined to have the following meanings:

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

*Aspergillus niger* is a filamentous fungi that has been widely utilized for enzyme production on commercial scale. In some embodiments, the ecm33 promoter is of an *Aspergillus* species. In some embodiments, the ecm33 promoter is of *Aspergillus niger*. In some embodiments, the ecm33 promoter is of *Aspergillus niger* strain ATCC 1015. In some embodiments, the ecm33 promoter comprises the nucleotide sequence of SEQ ID NO:1. In some embodiments, the gene of interest is heterologous to *Aspergillus niger* strain ATCC 1015. In some embodiments, the host cell is *Aspergillus niger* strain 1015.

In some embodiments, the medium suitable for expressing the gene of interest is a complex media, such as a rich media, such as potato dextrose broth (PBD).

Promoters are screened and identified using proteomics. Each candidate promoter is put in front of a glucosidase and tested for strength of production and secretion. They are tested in three different media and with different sugars. Unexpectedly, the ecm33 promoter showed twice the expression and secretion of the standard promoter of glucoamylase. Mitogen-activated protein kinases (MAPk) increases the expression from the ecm33 promoter. MAPk in *Aspergillus niger* is not usually considered in the fungal community, nor is heterozygous expression.

They put each candidate promoter in front of their favorite glucosidase and tested for strength of production and secretion. They tested in three different media and with different sugars. This is a sugar-induced promoter, with twice the expression and secretion of the gold standard (glucoamylase).

The nucleotide sequence of the *Aspergillus niger* strain ATCC 1015 ecm33 promoter is follows:

(SEQ ID NO: 1)
```
ATTGCTTGGAGTCCGATTTCAAGCTGCCGCATCGGCTCGAGCATCGTACA
CAAGCACTAGAAGCCTATGCTTGGTATGAATGGTCAGGACTTACTGAAAG
ACCGGGGAAGAAAGGGAAGAAGGGGGAGGAAGAGGAGCCAGAGGGCAG
GCAGAACGAATCAGCAGACGCATGAGCAAGAAGTTGGTCATTGGCGAGGT
GTTACAGGATGGAGCAGACTAAACCAAATGGACCGACCATTCGTTTCCAG
GACCAAGATCAGGATTCCTCGATTTCTTTTTCCGCTCTCCGTTACCGTGG
GCCAATCGCCCCTCGAAGTTAATTAATTAAACCCGGACAGGTACATGAAA
GTGAGTAAATTACGGTACGGGCAGCGTTCATACGCTGGTCCGGTAACGTC
GCAAGGAGAGAAAGGCGCCCCCCTCCCCGGTCTCAGGTCCACCAGCCTTT
TCGGGGCCACGACTCCTTTCTTGCCTTGGTTTGTCCTCCCTGAAAGTCTT
CCCACTTTCTTCTGAAGAAGATTTTCTTTTCCAGCCATCCAGTCCTTCTT
TTCCCTTTCCTCTCGTTTCTCTCGCTTTCCTCTGTCCTTCCCTTCTTC
TTTCCCCTTCTTCCCTTCCCGTGCAAATCGTGCCTGCCTAACCCGCGCAC
TTTCTCTCGCTGAGGGTCTTCGCTCATAAAGCTTCTCCTTCGTTGAAGCT
CTTCTCCATTCGCTCGCTCGCTTATTTATTGTCTCACAAACCCCCCTTCA
GCTCTTACGCTGCTATCCGTGTCAACAAAGGGCCTTGCCTCGCCCCAGTT
CGCATACTTGACCAACAGCCGTCATTGGTAGGTCAACCTCTTCATCAAGC
TGCTGTCTGATCTGTTTATCTTTTGCGCCTGCCACGACTGGGATTGGATC
TGTTGGATCGGAAGGGCCTTGGCAGTGATTTAGGAGCAGACGAAGCGAAC
ATTGGTGACTGACATCTTTTCGACTATACAGTCTCAAGTTATCCTAAGCA
```

The invention is useful in a biorefinery process using lignocellulose as a feedstock to produce fuels and chemicals.

REFERENCES CITED

1. Klein-Marcuschamer D, Oleskowicz-Popiel P, Simmons B A, Blanch H W. 2012. The challenge of enzyme cost in the production of lignocellulosic biofuels. Biotechnol Bioeng 109:1083-1087.
2. Naik S N, Goud V V, Rout P K, Dalai A K. 2010. Production of first and second generation biofuels: A comprehensive review. Renew Sustain Energy Rev.
3. Liu G, Zhang J, Bao J. 2016. Cost evaluation of cellulase enzyme for industrial-scale cellulosic ethanol production based on rigorous Aspen Plus modeling. Bioprocess Biosyst Eng.
4. D'haeseleer P, Gladden J M, Allgaier M, Chain P S G, Tringe S G, Malfatti S A, Aldrich J T, Nicora C D, Robinson E W, Paša-Tolić L, Hugenholtz P, Simmons B A, Singer S W. 2013. Proteogenomic Analysis of a Thermophilic Bacterial Consortium Adapted to Deconstruct Switchgrass. PLoS One 8.
5. Gladden J M, Park J I, Bergmann J, Reyes-Ortiz V, D'Haeseleer P, Quirino B F, Sale K L, Simmons B A, Singer S W. 2014. Discovery and characterization of ionic liquid-tolerant thermophilic cellulases from a switchgrass-adapted microbial community. Biotechnol Biofuels 7.
6. Schuster E, Dunn-Coleman N, Frisvad J, Van Dijck P. 2002. On the safety of *Aspergillus niger*—A review. Appl Microbiol Biotechnol.
7. Sewalt V, Shanahan D, Gregg L, La Marta J, Carrillo R. 2016. The Generally Recognized as Safe (GRAS) Process for Industrial Microbial Enzymes. Ind Biotechnol 12:295-302.
8. Punt P J, Van Biezen N, Conesa A, Albers A, Mangnus J, Van Den Hondel C. 2002. Filamentous fungi as cell factories for heterologous protein production. Trends Biotechnol.
9. Pel H J, De Winde J H, Archer D B, Dyer P S, Hofmann G, Schaap P J, Turner G, De Vries R P, Albang R, Albermann K, Andersen M R, Bendtsen J D, Benen J A E, Van Den Berg M, Breestraat S, Caddick M X, Contreras R, Cornell M, Coutinho P M, Danchin E G J, Debets A J M, Dekker P, Van Dijck P W M, Van Dijk A, Dijkhuizen L, Driessen A J M, D'Enfert C, Geysens S, Goosen C, Groot G S P, De Groot P W J, Guillemette T, Henrissat B, Herweijer M, Van Den Hombergh J P T W, Van Den Hondel C A M J J, Van Der Heijden R T J M, Van Der Kaaij R M, Klis F M, Kools H J, Kubicek C P, Van Kuyk P A, Lauber J, Lu X, Van Der Maarel M J E C, Meulenberg R, Menke H, Mortimer M A, Nielsen J, Oliver S G, Olsthoorn M, Pal K, Van Peij N N M E, Ram A F J, Rinas U, Roubos J A, Sagt C M J, Schmoll M, Sun J, Ussery D, Varga J, Vervecken W, Van De Vondervoort P J J, Wedler H, Wösten H A B, Zeng A P, Van Ooyen A J J, Visser J, Stam H. 2007. Genome sequencing and analysis of the versatile cell factory *Aspergillus niger* CBS 513.88. Nat Biotechnol 25:221-231.
10. Andersen M R, Salazar M P, Schaap P J, Van De Vondervoort P J I, Culley D, Thykaer J, Frisvad J C, Nielsen K F, Albang R, Albermann K, Berka R M, Braus G H, Braus-Stromeyer S A, Corrochano L M, Dai Z, Van Dijck P W M, Hofmann G, Lasure L L, Magnuson J K, Menke H, Meijer M, Meijer S L, Nielsen J B, Nielsen M L, Van Ooyen A J J, Pel H J, Poulsen L, Samson R A, Stam H, Tsang A, Van Den Brink J M, Atkins A, Aerts A, Shapiro H, Pangilinan J, Salamov A, Lou Y, Lindquist E, Lucas S, Grimwood J, Grigoriev I V., Kubicek C P, Martinez D, Van Peij N N M E, Roubos J A, Nielsen J, Baker S E. 2011. Comparative genomics of citric-acid-producing *Aspergillus niger* ATCC 1015 versus enzyme-producing CBS 513.88. Genome Res 21:885-897.
11. Baker S E. 2006. *Aspergillus niger* genomics: past, present and into the future. Med Mycol 44 Suppl 1:S17-21.
12. Park J I, Steen E J, Burd H, Evans S S, Redding-Johnson A M, Batth T, Benke P I, D'haeseleer P, Sun N, Sale K L, Keasling J D, Lee T S, Petzold C J, Mukhopadhyay A, Singer S W, Simmons B A, Gladden J M. 2012. A thermophilic ionic liquid-tolerant cellulase cocktail for the production of cellulosic biofuels. PLoS One 7.
13. Amaike Campen S, Lynn J, Sibert S J, Srikrishnan S, Phatale P, Feldman T, Guenther J M, Hiras J, An Tran Y T, Singer S W, Adams P D, Sale K L, Simmons B A, Baker S E, Magnuson J K, Gladden J M. 2017. Expression of 13. naturally ionic liquid-tolerant thermophilic cellulases in *Aspergillus Niger*. PLoS One 12.
14. Fowler T, Berka R M, Ward M. 1990. Regulation of the glaA gene of *Aspergillus niger*. Curr Genet 18:537-545.
15. Petersen K L, Lehmbeck J, Christensen T. 1999. A new transcriptional activator for amylase genes in *Aspergillus*. Mol Gen Genet 262:668-676.
16. Gouka R J, Hessing J G, Punt P J, Stam H, Musters W, Van den Hondel C a. 1996. An expression system based on the promoter region of the *Aspergillus awamori* 1,4-beta-endoxylanase A gene. Appl Microbiol Biotechnol 46:28-35.
17. Punt P J, Dingemanse M A, Kuyvenhoven A, Soede R D M, Pouwels P H, van den Hondel C A M J J. 1990. Functional elements in the promoter region of the *Aspergillus nidulans* gpdA gene encoding glyceraldehyde-3-phosphate dehydrogenase. Gene 93:101-109.
18. Punt P J, Kramer C, Kuyvenhoven A, Pouwels P H, Hondel C A M J J va. den. 1992. An upstream activating sequence from the *Aspergillus nidulans* gpdA gene. Gene 120:67-73.
19. Ferreira de Oliveira J M P, van Passel M W J, Schaap P J, de Graaff L H. 2011. Proteomic analysis of the secretory response of *Aspergillus niger* to D-maltose and D-xylose. PLoS One 6.
20. Minetoki T, Kumagai C, Gomi K, Kitamoto K, Takahashi K. 1998. Improvement of promoter activity by the introduction of multiple copies of the conserved region III sequence, involved in the efficient expression of *Aspergillus oryzae* amylase-encoding genes. Appl Microbiol Biotechnol.
21. Chiang Y M, Meyer K M, Praseuth M, Baker S E, Bruno K S, Wang C C C. 2011. Characterization of a polyketide synthase in *Aspergillus niger* whose product is a precursor for both dihydroxynaphthalene (DHN) melanin and naphtho-??-pyrone. Fungal Genet Biol 48:430-437.
22. Punt P J, Oliver R P, Dingemanse M A, Pouwels P H, van den Hondel C A M J J. 1987. Transformation of *Aspergillus* based on the hygromycin B resistance marker from *Escherichia coli*. Gene 56:117-124.
23. Su X, Schmitz G, Zhang M, Mackie R I, Cann I K O. 2012. Heterologous Gene Expression in Filamentous Fungi. Adv Appl Microbiol 81:1-61.
24. Lubertozzi D, Keasling J D. 2009. Developing *Aspergillus* as a host for heterologous expression. Biotechnol Adv.
25. Kitano H, Kataoka K, Furukawa K, Hara S. 2002. Specific expression and temperature-dependent expression of the acid protease-encoding gene (pepA) in *Aspergillus oryzae* in solid-state culture (rice-koji). J Biosci Bioeng 93:563-567.
26. Kulmburg P, Mathieu M, Dowzer C, Kelly J, Felenbok B. 1993. Specific binding sites in the alcR and alcA promoters of the ethanol regulon for the CREA repressor mediating carbon cataboiite repression in *Aspergillus nidulans*. Mol Microbiol 7:847-857.
27. Qiu R, Zhu X, Liu L, Tang G. 2002. Detection of a protein, AngCP, which binds specifically to the three upstream regions of glaA gene in *A. niger* T21. Sci China C Life Sci 45:527-537.
28. Aro N, Ilmén M, Saloheimo A, Penttil?? M. 2003. ACEI of *Trichoderma reesei* is a repressor of cellulase and xylanase expression. Appl Environ Microbiol 69:56-65.
29. Saloheimo A, Aro N, Ilmén M, Penttilä M. 2000. Isolation of the acel gene encoding a Cys2-His2 transcription factor involved in regulation of activity of the cellulase promoter cbh1 of *Trichoderma reesei*. J Biol Chem 275:5817-5825.
30. Takada H, Nishida A, Domae M, Kita A, Yamano Y, Uchida A, Ishiwata S, Fang Y, Zhou X, Masuko T, Kinoshita M, Kakehi K, Sugiura R. 2010. The cell surface protein gene ecm33+ is a target of the two transcription factors Atf1 and Mbx1 and negatively regulates Pmk1 MAPK cell integrity signaling in fission yeast. Mol Biol Cell 21:674-685.
31. Ouyang H, Chen X, Lü Y, Wilson I B H, Tang G, Wang A, Jin C. 2013. One single basic amino acid at the ω-1 or ω-2 site is a signal that retains glycosylphosphatidylinositol-anchored protein in the plasma membrane of *Aspergillus fumigatus*. Eukaryot Cell 12:889-99.
32. Zhang J, Astorga M A, Gardner J M, Walker M E, Grbin P R, Jiranek V. 2018. Disruption of the cell wall integrity gene ECM33 results in improved fermentation by wine yeast. Metab Eng 45:255-264.
33. Gil-Bona A, Monteoliva L, Gil C. 2015. Global Proteomic Profiling of the Secretome of *Candida albicans* ecm33 Cell Wall Mutant Reveals the Involvement of Ecm33 in Sap2 Secretion. J Proteome Res 14:4270-4281.
34. Champer J, Ito J I, Clemons K V, Stevens D A, Kalkum M. 2016. Proteomic Analysis of Pathogenic Fungi Reveals Highly Expressed Conserved Cell Wall Proteins. J fungi 2:6.
35. Yin X, Shin H D, Li J, Du G, Liu L, Chen J. 2017. Comparative genomics and transcriptome analysis of *Aspergillus Niger* and metabolic engineering for citrate production. Sci Rep 7.
36. Gil-Bona A, Reales-Calderon J A, Parra-Giraldo C M, Martinez-Lopez R, Monteoliva L, Gil C. 2016. The cell wall protein Ecm33 of *Candida albicans* is involved in chronological life span, morphogenesis, cell wall regeneration, stress tolerance, and host-cell interaction. Front Microbiol 7.
37. Martinez-Lopez R, Monteoliva L, Diez-Orejas R, Nombela C, Gil C. 2004. The GPI-anchored protein CaEcm33p is required for cell wall integrity, morphogenesis and virulence in *Candida albicans*. Microbiology 150:3341-3354.
38. Romano J, Nimrod G, Ben-Tal N, Shadkchan Y, Baruch K, Sharon H, Osherov N. 2006. Disruption of the *Aspergillus fumigatus* ECM33 homologue results in rapid conidial germination, antifungal resistance and hypervirulence. Microbiology 152:1919-1928.
39. Pardo M, Monteoliva L, Vázquez P, Martinez R, Molero G, Nombela C, Gil C. 2004. PST1 and ECM33 encode two yeast cell surface GPI proteins important for cell wall integrity. Microbiology 150:4157-4170.
40. Koda A, Bogaki T, Minetoki T, Hirotsune M. 2006. 5′ untranslated region of the Hsp12 gene contributes to efficient translation in *Aspergillus oryzae*. Appl Microbiol Biotechnol.
41. Koda A, Minetoki T, Ozeki K, Hirotsune M. 2004. Translation efficiency mediated by the 5′ untranslated region greatly affects protein production in *Aspergillus oryzae*. Appl Microbiol Biotechnol.
42. Szewczyk E, Nayak T, Oakley C E, Edgerton H, Xiong Y, Taheri-Talesh N, Osmani S a, Oakley B R, Oakley B. 2006. Fusion PCR and gene targeting in *Aspergillus nidulans*. Nat Protoc 1:3111-20.
43. Colot H V., Park G, Turner G E, Ringelberg C, Crew C M, Litvinkova L, Weiss R L, Borkovich K A, Dunlap J C. 2006. A high-throughput gene knockout procedure for

9

44. Yelton M M, Hamer J E, Timberlake W E. 1984. Transformation of *Aspergillus nidulans* by using a trpC plasmid. Proc Natl Acad Sci USA 81:1470-1474.
45. Ward M, Lin C, Victoria D C, Fox B P, Fox J A, Wong D L, Meerman H J, Pucci J P, Fong R B, Heng M H, Tsurushita N, Gieswein C, Park M, Wang H. 2004. Characterization of humanized antibodies secreted by *Aspergillus niger*. Appl Environ Microbiol 70:2567-2576.
46. Livak K J, Schmittgen T D. 2001. Analysis of relative gene expression data using real-time quantitative PCR and the 2(−Delta Delta C(T)) Method. Methods 25:402-408.
47. Bok J W, Keller N P. 2012. Fast and easy method for construction of plasmid vectors using modified quick-change mutagenesis. Methods Mol Biol 944:163-74.

Neurospora reveals functions for multiple transcription factors. Proc Natl Acad Sci USA 103:10352-10357.

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

The invention having been described, the following examples are offered to illustrate the subject invention by way of illustration, not by way of limitation.

Example 1

Over 30 different prokaryotic and eukaryotic cellulase genes are introduced into *A. niger* to improve the enzyme production compared to bacterial production hosts. To do this, the promoter of the glucoamylase encoding gene, glaA, is used. The glaA promoter has traditionally been used in filamentous fungi to induce high levels of the heterologous gene expression in the presence starch. However the glaA promoter is not useful when growing *A. niger* in media lacking starch or maltose. Identification of constitutive promoters would enable enzyme production in a broader range of media, including media containing sugars derived form lignocellulosic biomass. Proteomic analysis of the *A. niger* secreome grown on a variety of carbon sources is conducted and over 40 promoters that may be used as genetic to drive heterologous enzyme production in *A. niger* are identified. Eight promoters out of the forty are integrated at the glaA location in chromosome 6 of the *A. niger* 11414 strain. The eight promoters (1 kb upstream from the start codon) are characterized for expression in media containing three different carbon sources: maltose, glucose, and xylose. One of the promoters, the promoter of the ecm33 gene, encoding cell wall protein Ecm33 (extracellular mutant 33) showed the equivalent or more enzyme production under all three media, compared to the glaA promoter, indicating that it is a constitutive promoter. These results demonstrate that the ecm33 promoter is a useful genetic tool for enzyme production in *A. niger*.

Over thirty prokaryotic and eukaryotic cellulases are identified and determined the function in the presence of ILs. These cellulases have been introduced into *A. niger* and compared the enzyme production and activity to *E. coli* which is a suitable expression host for enzyme production. The results indicate that strong genetic parts are required for the heterologous enzyme production, such as the promoter. This invention supports further genetic mutations for heterologous enzyme production in *A. niger*.

Glucoamylase gene, glaA promoter region have been utilized for expression of targeted enzymes or metabolites in filamentous fungi. However, the glaA promoter is inducible type promoter to express target gene at higher level and is required presence of starch, especially maltose in the fungal growth media. This invention allows us to choose the best promoter in different condition and optimize the enzyme production in filamentous fungi.

The promoter candidates are identified by proteomics, and most of them did have capability to drive heterologous gene expression. However, the promoter of ecm33 stood out from the rest. The gene of Ecm33 has been widely studied, but herein the promoter of Ecm33 is tested, excluding the coding region of the ecm33 gene.

Of the other promoters tested, the comparison of strength of promoters is dependent on the growth condition. Since some are maltose inducible, some are xylose inducible, and some are not inducible but weakly constitutive.

The 1 kb promoter of the Ecm33 gene is linked to for heterologous gene expression. The Ecm33 promoter is not sugar inducible and behaves as a constitutive promoter. Unexpectedly, the Ecm33 promoter is a stronger promoter than all of the other promoters tested.

Example 2

*Aspergillus niger*, an ascomycete filamentous fungus, is known to produce high levels of citric acid and other useful metabolites. The fungus also has a capability to secrete high levels of enzymes, making it a good candidate to develop into a high titer native and heterologous enzyme expression host for the production of enzymes relevant to lignocellulosic biofuel and bioproducts. In previous studies, several recombinant thermophilic bacterial cellulase enzymes were introduced into *A. niger* and demonstrated that the fungus is a suitable expression host for these enzymes. Here, we explored genetics parts to improve heterologous enzyme expression in *A. niger* and characterized promoters, based on secretome analysis of growth media. Eight promoters were picked and further elucidated their expression strength with a thermophilic beta-glucosidase, A5IL97, isolated from *Thermotoga petrophila*. A promoter of cell wall protein, Ecm33, significantly increases A5IL97 mRNA and protein expression under three different carbon source media. Some of these expressions were higher than gpdA and glaA promoters which are widely used in genetic engineering in *Aspergillus* and other filamentous fungi. Further characterization of ecm33 promoter revealed that a transcriptional factor, AtfA, playing downstream of MAPK signaling cascade of calcium ion channel, binds the ecm33 promoter in vivo. These results showed the useful genetics part for heterologous enzyme production and other genetic engineering in *A. niger* which support high titer production of heterologous enzymes for lignocellulolytic biofuel and renewable chemical production.

A number of inducing and constitutive promoters have been reported and utilized to improve the expression levels of products derived from microbes. A filamentous fungus, *A. niger* has been used for native and heterologous enzyme production as a versatile cell factory. Previous studies show potential for improving enzyme production through genetic engineering. This study identified 8 promoters through fungal secretome analysis under different carbon sources and characterized a novel promoter region of ecm33 for heterologous enzyme production in *A. niger*. The results demonstrated to enhance heterologous enzyme expression, binding by a transcriptional factor, AtfA, involving in MAPK signaling pathway which advance recombinant enzyme and protein productions in the fungus.

In this study, we performed proteomics analysis from the fungal secretome, incubated under different carbon source growth conditions to identify the promoter for establishing heterologous expression systems in *A. niger*. We picked promoter regions of 20 highest genes from the proteomics results and further characterized the expression strength of the promoter regions with the bacterial gene, A5IL97. One of the screened promoters, ecm33, expresses A5IL97 higher than that of gpdA which is the primarily used constitutive promoter for functional genetics studies in *Aspergilli*. Furthermore, we elucidate that ecm33 promoter region is bound by a transcriptional factor, AtfA, which is involved in the Pmk1 mitogen-activated protein kinase (MAPK) signaling pathway. These results show a novel genetics promoter tool and its regulation for heterologous enzyme expression in *A. niger*.

Results
Proteomics Results

Through the secreted protein from the culture filtrates results, we picked 8 most secreted proteins and utilize screening of the promoters, which could enhance the heterologous expression; GlaA, PepA, Ecm33, GpdA, Rnt2, AgdA, Ast1, and Sed2. GlaA encodes starch-degrading enzyme glucoamylase and has been widely utilized for gene manipulation in filamentous fungi. PepA encodes aspartyl protease and controlled by temperature. Ecm33 encodes GPI-anchored cell protein, including carbohydrate binding domain, called WSC domain. GpdA encodes glyceralodehyde-3-phosphate dehydrogenase (GAPDH) and has been widely used as constitutive promoter in yeast and filamentous fungi. Rnt2 encodes ribonuclease T2 family protein. AgdA encodes α-glucosidase in glycoside hydrolase family 31 and has been known to secrete most under maltose condition, used as a promoter in *A. oryzae* (19, 20). Sed2 encodes tripeptidyl peptidase.

Creation of Promoter Mutants from Proteomics Analysis

In order to increase gene targeting efficiency for screening promoter mutants, the first goal was to obtain kusA deletion mutant of ATCC11414 *A. niger*. We utilized uracil/uridine auxotrophy ATCC11414 mutant, KB1002 (21) to replace the full length of the open reading frame (ORF) kusA by *A. fumigatus* pyrG (FIG. 1). One hundred fifty mutants were DNA extracted and screened by PCR, and then thirteen PCR-positive mutants were further digested with two restriction enzymes, XhoI and EcoNI and screened by Southern blots (FIG. 1). Six mutants were confirmed by Southern blot and one of these strains, mutant #18 was chosen as a parental strain for creating promoter mutants.

Figure 2:
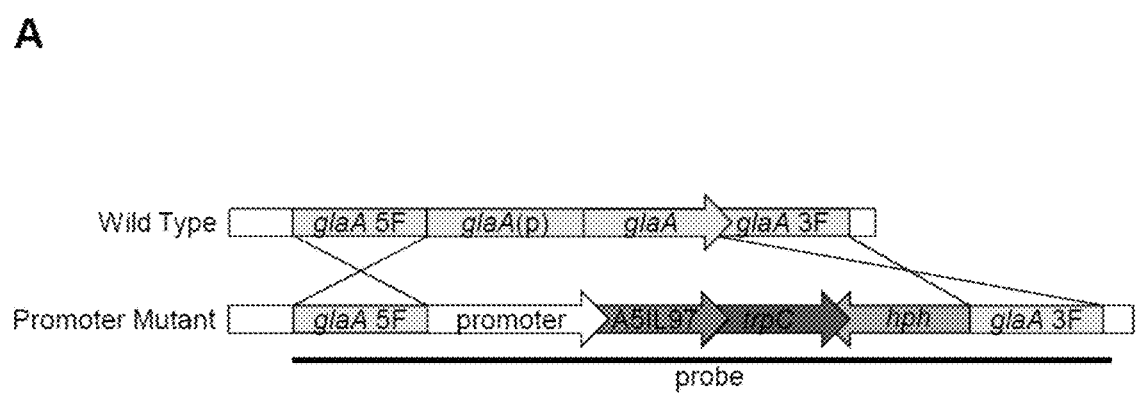
FIG. 2. Schematic diagram of promoter mutants and Southern blot of promoter A mutants (glaA) mutants. Panel A. Diagram of *A. niger* glaA ORF replaced by over-expression A5IL97 construct cassette with different promoters. Mutants were confirmed by Southern blot using approximately 6.5 kb of probe with two different restriction enzymes. Panel B. Southern blot confirmation for glaA promoter mutants. The NheI digestion showed 2.9 kb and 5.3 kb fragments in wild type (Lane 1) and a 9.7 kb fragment in glaA promoter strain (Lane 2).
Figure 8:
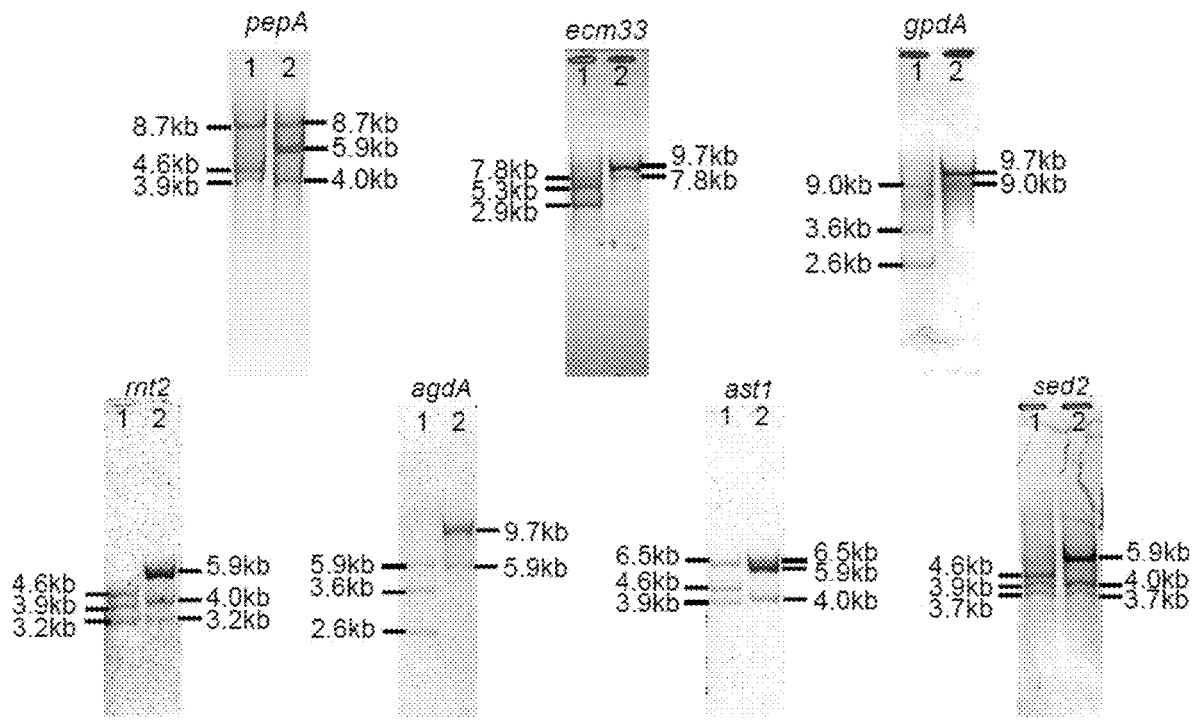
FIG. 8. Southern blot of promoter mutants. All promoter mutants were confirmed by Southern blot and compared to wild type. Each Southern blot showed Lane 1: wild type, Lane 2: promoter mutant. The expected band sizes are following: pepA mutant digested by SphI: wild type=3.9 kb, 4.6 kb, and 8.7 kb, mutant=4.0 kb, 5.9 kb, 8.7 kb; ecm33 mutant digested by NheI: wild type=2.9 kb, 5.3 kb, and 7.3 kb, mutant=7.8 kb, 9.7 kb; gpdA mutant digested by BamHI: wild type=2.6 kb, 3.6 kb, and 9.0 kb, mutant=9.0 kb, and 9.7 kb; rnt2 mutant digested by SphI: wild type=3.2 kb, 3.9 kb, and 4.6 kb, mutant=3.2 kb, 4.0 kb, and 5.9 kb; agdA mutant digested by BamHI: wild type=2.6 kb, 3.6 kb, and 5.9 kb, mutant=5.9 kb, 9.7 kb; ast1 mutant digested by SphI: wild type=3.9 kb, 4.6 kb, and 6.5 kb, mutant=4.0 kb, 5.9 kb, and 6.5 kb; sed2 mutant digested by SphI: wild type=3.7 kb, 3.9 kb, and 4.6 kb, mutant=3.7 kb, 4.0 kb, and 5.9 kb.

For promoter mutants, codon-optimized A5IL97 (GenBank Accession: KY014108) was used to measure each promoter strength. The hygromycin gene, hph, was utilized for fungal transformation (22). After the transformation, at least five transformants for each promoter were obtained, their DNA extracted, and screened by PCR and Southern blots. As shown in FIG. 2, the deletion of kusA mutants enhanced homologous integration of promoter constructs to native glaA locus. Most obtained transformants were positive through PCR and Southern blots screening (FIG. 2, FIG. 8). Three mutants of each promoter were chosen and initially analyzed for their morphology and enzyme activity of A5IL97. These strains with the same promoter did not exhibited clear differences in fungal morphology and enzyme activity. Then, one of these each promoter mutants were chosen for further studies.

All *A. niger* strains, *E. coli* strains, and plasmids used in this study are available at the Joint BioEnergy Institute under the Inventory of Composable Elements (ICE) system. All data generated or analyzed during this study are included in the manuscript and additional materials.

Promoter Screenings with A5IL97

Figure 3:
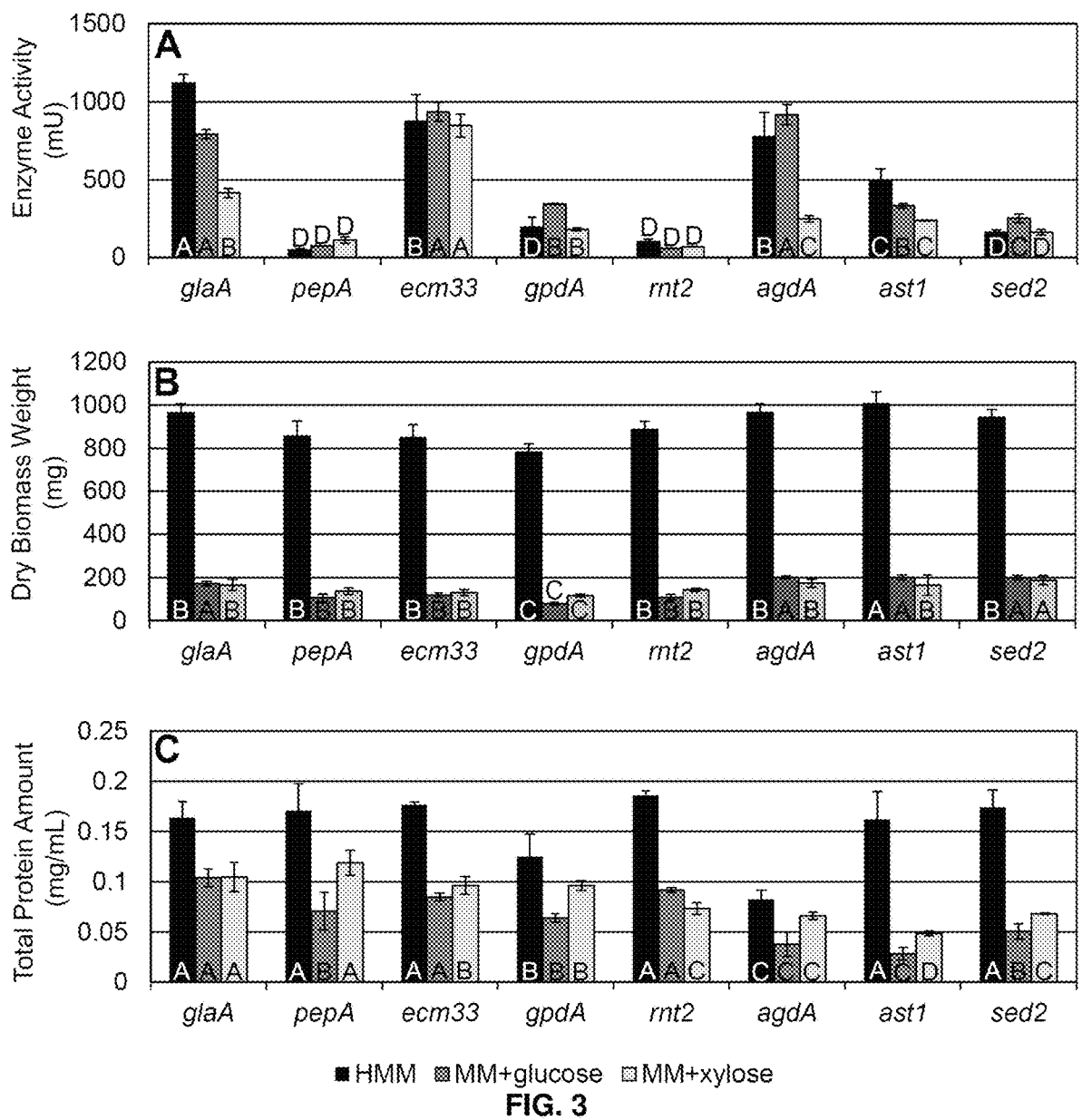
FIG. 3. Comparison of relative enzyme activity, biomass activity, total protein amount in 8 promoter mutants. Panel A. Relative enzyme activity was measured using pNPG and normalized to those of glaA promoter activity under three different media conditions, HMM, MM plus glucose (MM+glucose), and MM plus xylose (MM+xylose). Panel B. Dry fungal biomass was measured and calculated the biomass activity as enzyme activity (mU) per the dry biomass (mg dry weight). Panel C. Total protein concentrations were measured under three different media conditions using Bradford method. Each alphabet indicated differences between strains that were statistically significant (P<0.05) according to Student's t-test each comparison. Error bars showed the standard deviations of three replications.
Figure 9:
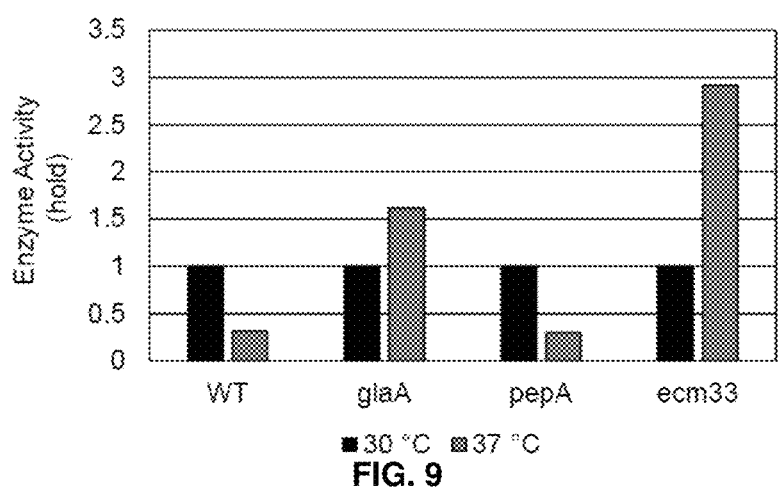
FIG. 9. Temperature impact to promoter mutants. Each promoter mutants were incubated with CSL-fructose media for 24 hrs, then further incubated with HMM media for 48 hrs. The enzymatic activity at 30° C. was set to 1 and calculated relative enzymatic activity with those at 37° C.

After the mutant confirmation, each promoter mutant was pre-incubated under CSL-fructose media and then transferred to three different carbon sources; 12% maltose (HMM), 10% glucose (MM plus glucose), and 10% xylose (MM plus xylose) to measure biomass production, β-glucosidase activity from A5IL97, and total protein production (FIG. 3, FIG. 9). For reference, wild type 11414 strain is capable to produce about 1.4 mU of native beta-glucosidases at 37° C. and about 10 mU at 30° C. with HMM media, following the same incubation method (FIG. 9) and about 1 mU under MM plus glucose or xylose media at 30° C. (data not shown). The result of enzyme activity was directly linked with the strength of the promoter to activate downstream enzymatic gene, A5IL97. The glaA promoter region has been known as a promoter, induced by maltose, starch, and glucose with low concentration, but repressed by xylose (23, 24); the result was replicated in our work. The enzyme activity with the glaA promoter is induced by HMM, is relatively induced by MM plus glucose, and is repressed by MM plus xylose. Interestingly, promoter agdA showed high enzyme activity under HMM and MM plus glucose media as well as promoter ecm33 under all three media (FIG. 3). Previous study also showed the promoter region of pepA is controlled by temperature in *A. oryzae* (25); again the result was repeated in our work in *A. niger* (FIG. 9). The result also showed that the glaA and ecm33 promoters increased their enzyme activity at 37° C. incubation, which are approximately 1.5-fold and 3-fold more activity than at 30° C., respectively. All promoters produced more biomass under HMM media, as compared to the other two media (FIG. 3). All promoters also showed the highest total protein production under HMM media. The agdA promoter showed less total protein amount under HMM media, compared to other promoters. Other secretome study showed that agdA is one of the most abundant proteins under maltose (19) which our proteomics showed the same result, however agdA promoter produced less total protein, compared to others (FIG. 3). To investigate A5IL97 protein production out of total protein amount, we also performed the SDS-PAGE from 20× concentrated each promoter incubated cultures. The expected A5IL97 size was approximately 52 kDa and some promoters showed the expression (FIG. 4). These promoter screening results showed that ecm33 promoter acts as a constitutive expression promoter under three carbon source media.

To further investigate ecm33 promoter strength, we performed the A5IL97 gene expression study by quantitative real-time (qRT)—PCR under 3 different cultures with 2 different time-points. As previously described, glaA promoter mutant showed the different levels of the A5IL97 expression under three media; maltose (HMM) induced the most expression at 48 hrs, but glucose and xylose (MM plus glucose or xylose) induced less expression with 1.8-fold and 1.3-fold differences at 48 hrs, respectively (FIG. 5). Interestingly, ecm33 promoter showed increasing A5IL97 expression significantly under MM plus glucose and MM plus xylose. Under maltose inducing condition, the promoter of ecm33 (1.7-fold) with A5IL97 was relatively equivalent strength as glaA promoter (2.7-fold) (FIG. 5). These results combined to show that ecm33 promoter is promising for increasing heterologous enzyme expression. This led to more questions about the gene regulatory network behind the ecm33 promoter and we further investigated the binding motif by transcriptional factors.

AtfA Binds Ecm33 Promoter Region

Figure 6:
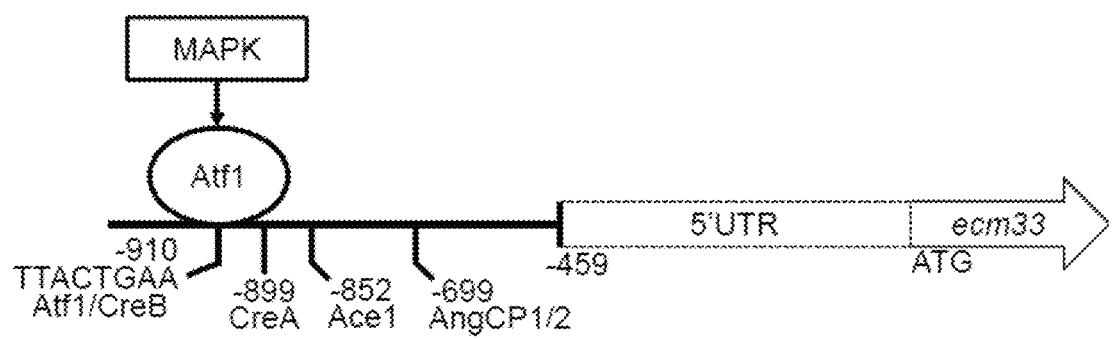
FIG. 6. Protein purification and gel shift assay. Panel A. Protein purification of AtfA, expressed in BL21 (DE3) of *E. coli*. Each lane represented M: marker, 1: flow-through 2 and 3: wash resin with Tris-HCl, pH8.0 with 300 mM sodium chloride and 15 mM imidazole, 4 and 5: wash resin with Tris-HCl, pH8.0 with 300 mM sodium chloride and 45 mM imidazole, 6 and 8: first elution with Tris-HCl, pH8.0 with 300 mM sodium chloride and 300 mM imidazole, 7 and 9: second elution with the same buffer as lanes 6 and 8. Black arrows indicated the expected AtfA protein size. Panel B. Gel shift assay showed AtfA protein binding at ecm33 promoter region specific site of yeast (Y): TTACTGAA and fungi (F): TTACAGTAA, but not mutated (M): CCGCGCGC.
Figure 7:
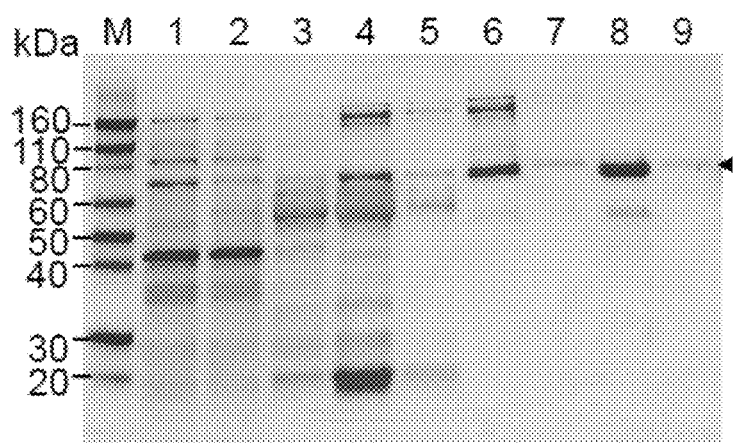
FIG. 7. AtfA involvement in ecm33 promoter region. A model of AtfA regulation binding ecm33 promoter and MAPK signaling pathway. Binding site AtfA for fungi, TTACTGAA or yeast, TTACAGTAA (30), located at ecm33 promoter region enhanced A5IL97 or possibly other heterologous gene expression.
Figure 7:
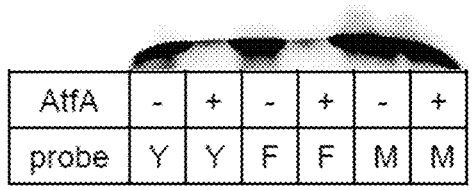

The promoter region of glaA promoter contains several essential binding motif, by transcriptional factors, CreA (C/G-C/T-GG A/G G; (26)), AmyR (CGG-N6-CGG (SEQ ID NO: 2); (15)), AngCP1 and AngCP2 (CCAAT; (27)) and ACE1 (AGGCA; (28, 29)). A putative Atf1/CreB-binding site and Mbx1/Rim1-binding site have been located on the promoter region of ecm33 in *Saccharomyces pombe*, which is linked with Ecm33 under the negative regulation of Pmk1 MAPK pathway, associated with calcium ion channel signaling (30). To address the hypothesis of whether any transcriptional factors bind ecm33 promoter region that enhance the heterologous expression, we searched the putative Atf1/CreB binding-site and other potential binding-sites by other transcriptional factors on ecm33 promoter region (FIG. 6). The results showed that ecm33 promoter in *A. niger* contained a similar binding site as Atf1, TTACTGAA, which has been reported in ecm33 promoter of *S. pombe*; TTACAGTAA (30). We investigated whether Atf1 homologs, AtfA in *A. niger*, is capable to bind the potential binding motif, TTACTGAA, located at ecm33 promoter. Two different binding motifs, as described above along with mutated motif, CCGCGCGC were tested with purified AtfA protein and confirmed the bindings in vivo (FIG. 7).

Discussion

Here, we found promoter candidates through fungal secretome and identified a novel promoter, ecm33, which was constitutive expression under maltose, glucose, and xylose media condition. Ecm33 has been previously studied that the gene is located in plasma membrane (31) and involved in membrane transporter for carbohydrate (32) and secretion pathway (33). This could explain that Ecm33 has been reported one of the most secreted proteins in *A. niger* cultures (19, 34, 35). In addition, Ecm33 is required for crucial biological functions such as cell wall integrity, morphogenesis, stress tolerance, and virulence in *Saccharomyces pombe*, *Aspergillus fumigatus*, and, *Candida albicans* (30, 36-38). The clear function of Ecm33 in *A. niger* is still unknown, however, a paralog of Ecm33, Pst1 has been reported that the gene increases the expression to protect fungal cell wall to lower pH culture media during the fermentation (35, 39). These previous studies combined to hypothesize that Ecm33 in *A. niger* could be an important for various biological function which duplicated the role with Pst1, hence the gene is required to possess strong constitutive promoter.

To understand the ecm33 promoter, we identified that a transcriptional factor, AtfA bound a specific motif, TTACT-GAA at the ecm33 promoter region (FIG. 6). Binding motifs by several other transcriptional factors, which have been known to bind the glaA promoter region, were identified (27, 29); hence the ecm33 promoter region could be good for expression. These transcriptional factors, except CreA were not fully explored to understand the function in *A. niger* and it is necessary to understand how these transcriptional factors play roles, regarding to the promoter regulatory network. In addition, approximately 1000 bp of ecm33 promoter region, used in this study contains about 459 bp of 5 prime untranslated regions (5'UTR), however, it is generally accepted that 5UTR has been known to affect translation efficiency in *A. oryzae* (40, 41) and may improve translation of the heterologous protein. Taken together, the functional analysis of ecm33 promoter by truncation and mutation is necessary to understand the effect of MAPK signaling pathway through AtfA binding to ecm33 promoter and 5UTR impact to translation.

Overall, the findings in the present study revealed that ecm33 promoter identified through secretome analysis in *A. niger*, acted a constitutive promoter under maltose, glucose, and xylose growth condition and bound by a transcriptional factor, AtfA under the MAPK signaling pathway regulation. Although cis-element motif of ecm33 promoter was defined, additional work is required to elucidate the regulatory mechanisms and the translational process for improving heterologous enzyme expression in *A. niger*.

Materials and Methods

Fungal Strains and Growth Conditions

*Aspergillus niger* ATCC® 11414™ obtained from the American Type Culture Collection (Manassas, Va.) was used to generate the mutants in this study and listed in Table 1. All strains were maintained as glycerol stocks and grown at 30° C. on minimal media or potato dextrose agar media (PDA).

TABLE 1

Strain used in this study.

| Strain | Genotype | Protein ID[a] | Annotations | Reference |
|---|---|---|---|---|
| wild type | ATCC11414 | | | |
| A5IL97 | glaA(p)::A5IL97::trpC, hph | | | Amaike Campen et al. 2017 |
| KB1002 | pyrG- | | | Chiang Y M et al. 2011 |
| ΔkusA | pyrG-, ΔkusA::*A. fumigatus* pyrG | | | this study |
| glaA | pyrG-, ΔkusA::*A. fumigatus* pyrG, glaA(p)::A5IL97::*A. nidulans* trpC::hph | 1166799 | glucoamylase | this study |
| pepA | pyrG-, ΔkusA::*A. fumigatus* pyrG, pepA(p)::A5IL97::*A. nidulans* trpC::hph | 1141688 | aspartyl protease | this study |
| ecm33 | pyrG-, ΔkusA::*A. fumigatus* pyrG, ecm33(p)::A5IL97::*A. nidulans* trpC::hph | 1146364 | GPI-anchored cell protein | this study |
| gpdA | pyrG-, ΔkusA::*A. fumigatus* pyrG, gpi/A(p)::A5IL97::*A. nidulans* trpC::hph | Z32524[b] | glyceraldehyde-3-phosphate dehydrogenase | this study |

TABLE 1-continued

Strain used in this study.

| Strain | Genotype | Protein ID[a] | Annotations | Reference |
|---|---|---|---|---|
| rnt2 | pyrG–, ΔkusA::*A. fumigatus* pyrG, rnt2(p)::A5IL97::*A. nidulans* trpC::hph | 1142610 | ribonuclease T2 | this study |
| agdA | pyrG–, ΔkusA::*A. fumigatus* pyrG, agdA(p)::A5IL97::*A. nidulans* trpC::hph | 1146704 | α-glucosidase | this study |
| ast1 | pyrG–, ΔkusA:: *A. fumigatus* pyrG, ast1(p)::A5IL97::*A. nidulans* trpC::hph, | 1146675 | aspartate aminotransferase | this study |
| sed2 | pyrG–, ΔkusA::*A. fumigatus* pyrG, sed2(p)::A5TL97::*A. nidulans* trpC::hph | 1155990 | tripeptidyl-peptidase | this study |

Protein ID numbers were reference in *Aspergillus niger* ATCC1015 v.4.0 genome information in Joint Genome Institute (US DOE, Walnut Creek, CA) website (10)(11)[a].
The strain of gpdA promoter was derived from *Aspergillus nidulans* gpdA region with the NCBI accession number[b].

Proteomics

ATCC11414 and thermophilic bacterial β-glucosidase encoding gene, A5IL97, randomly integrated strains were used (13). Both strains were pre-incubated at 37° C., 200 rpm under CSL-frucrose media for 24 hrs and switched to several carbon source media for further 48 hrs.

Fusion PCR and Strain Manipulation i) ΔkusA in ATCC11414

To create different promoter genes with heterologously expressed A5IL97, kusA, orthologs of ku70 and nkuA, was replaced with *A. fumigatus* pyrG in KB1002 (21). The replacement of kusA ORF was constructed using fusion PCR method, following previously described method (42). All primer sequences used in this study were listed in Table 2. Briefly, about 1.2 kb upstream and downstream of kusA ORF were amplified with primers, kusA5FFor and kusA5FRev for the upstream and kusA3FFor and kusA3FRev for the downstream from wild type genomic DNA (gDNA). Then, approximately 1.7 kb of *A. fumigatus* pyrG was amplified with AFpyrGFor and AFpyrGRev primers from pCDS60 (43). All three PCR products were fused and amplified with kusA5FFornested and kusA3FRevnested primers and Phusion high-fidelity DNA polymerase (Thermo Fisher Scientific, Waltham, Mass.), following the manufactures instructions. Final PCR fragment was confirmed by restriction enzymes and sequencing. Five micrograms of the PCR fragment was introduced into KB1002 to create ΔkusA strain, following the standard fungal transformation method using polyethylene glycol (44). Transformants were initially screened using 1) kusAORFintFor and kusAORFintRev primers for checking kusA ORF deletion and 2) AFpyrGORFFor and kusA3FRev primers for checking the fusion PCR homologous integration to targeted kusA region. After PCR screening, the mutants were further confirmed by Southern hybridization analysis using North2South™ Chemiluminescent Hybridization and Detection kit (Thermo Fisher Scientific, Waltham, Mass.). The probe for Southern was amplified using kusA5FFor and kusA3FRev primers from wild type gDNA and created, following North2South™ Biotin Random Primer DNA labeling kit manufacturer's instructions (Thermo Fisher Scientific, Waltham, Mass.) (FIG. 1).

Table 2. Oligonucleotide sequence used in this study. Bold characters mean estimated binding site of AtfA.

TABLE 2

| Primer | Sequence (5'-3') |
|---|---|
| kusA5FFor | CCGATTCCTCCATTTCCACAGC (SEQ ID NO: 3) |
| kusA5FFornested | CATTCAGAGAGCTACCCGTAG (SEQ ID NO: 4) |
| kusA5FRev | CTCCTTCAATATCATCTTCTGTCAGTAGAATGTTGTGGAATCGTTTAAAGC (SEQ ID NO: 5) |
| kusA3FFor | ATCCACTTAACGTTACTGAAATCCATGGCGGGATTGTTGGATTCGCTAGTG (SEQ ID NO: 6) |
| kusA3FRev | GCAGAGATATTTGAGGGCACC (SEQ ID NO: 7) |
| kusA3FRevnested | CTTACGATGCAAGATGAATACGA (SEQ ID NO: 8) |
| AFpyrGFor | GACAGAAGATGATATTGAAGGAG (SEQ ID NO: 9) |
| AFpyrGRev | GATTTCAGTAACGTTAAGTGGAT (SEQ ID NO: 10) |
| AFpyrGORFFor | GTCGATGTGTGTCTTGATGAC (SEQ ID NO: 11) |
| kusAORFintFor | GCGTTTGTTCATCATAACCGAC (SEQ ID NO: 12) |

TABLE 2-continued

Oligonucleotide sequence used in this study. Bold characters mean estimated binding site of AtfA.

| Primer | Sequence (5'-3') |
|---|---|
| kusAORFintRev | GGGTATTTGAGAGGCTCGTAC (SEQ ID NO: 13) |
| promoterFor | GGTACCCTACCAATGCTCTCG (SEQ ID NO: 14) |
| promoterRev | GAAGAGCATGGCTCCTCATCC (SEQ ID NO: 15) |
| glaAORFintFor | GTCAGTCACCGTCGCGGTCGACGTTC (SEQ ID NO: 16) |
| glaAORFintRev | GCCATCCTGAATAACATCGGG (SEQ ID NO: 17) |
| A5IL97qPCRFor | TCGGTTCATGCACCAGTTTAAC (SEQ ID NO: 18) |
| A5IL97qPCRRev | CGAACTTGACGAGATGACCAC (SEQ ID NO: 19) |
| actinqPCRFor | CGTAAGGATCTGTACGGCAAC (SEQ ID NO: 20) |
| actinqPCRRev | CTTGGAGATCCACATCTGCTG (SEQ ID NO: 21) |
| Atf1ExpressionFor | CACAAGTTTGTAAGGAGAAGCAGGCTATGTCTGCGGCTGT TACTTCGACCG (SEQ ID NO: 22) |
| Atf1ExpressionRev | CACCACTTTGTACAAGAAAGCTGGTC (SEQ ID NO: 23) |
| EMSAAtf1fungiFor | CCGTCGTAGCCCCTGAGCAGGGATA GTCAGGATTACTGAAAGACCG (SEQ ID NO: 24) |
| EMSAAtf1fungiRev | CGGTCTTTCAGTAAGTCCTGAC (SEQ ID NO: 25) |
| EMSAAtf1yeastFor | GTCAGGATTACAGTAAAGACCG (SEQ ID NO: 26) |
| EMSAAtf1yeastRev | CGGTCTTTACTGTAAGTCCTGAC (SEQ ID NO: 27) |
| EMSAmutatedFor | GTCAGGACCGCGCGCAGACCG (SEQ ID NO: 28) |
| EMSAmutatedRev | CGGTGTGCGCGCGGTCCTGAC (SEQ ID NO: 29) | ii) Promoter Mutants with A5IL97

The plasmid constructs with different promoter genes with heterologously expressed A5IL97, were synthesized by Joint Genome Institute, JGI (USA DOE, Walnut Creek, Calif.) and GenScript (Township, N.J.). Approximately 1000 bp of upstream of glaA promoter region, 1000 bp of different promoters, selected from secretome result, glaA propeptide, A5IL97, A. nidulans trpC terminator, hygromycin B resistant gene, hph, downstream of glaA region were fused and inserted into pUC57 plasmid. All promoters were designed to integrate to glaA native locus, along with replacing glaA ORF with A5IL97 as a control. PCR products were amplified with promoterFor and promoterRev primers using Phusion high-fidelity DNA polymerase (Thermo Fisher Scientific, Waltham, Mass.), following the manufactures instructions. Final PCR fragment was confirmed by restriction enzymes and sequencing. Five micrograms of the PCR fragment was transformed into ΔkusA strain, following previously described method (44). Each transformant with different promoter genes were initially screened using glaAORFintFor and glaAORFintRev primers for checking glaA ORF deletion and the fusion PCR homologous integration to targeted glaA region. The mutants were further screened, followed by Southern hybridization using North2South™ Chemiluminescent Hybridization and Detection kit (Thermo Fisher Scientific, Waltham, Mass.). The probe for Southern was amplified using promoterFor and promoterRev primers from each plasmid gDNA and created, following North2South™ Biotin Random Primer DNA labeling kit manufacturer's instructions (Thermo Fisher Scientific, Waltham, Mass.) (FIG. 2, FIG. 8).

Growth Condition of Mutants

Fresh conidia spores were collected from each mutant and inoculated with $10^6$ spores/ml to 50 ml of CSL-fructose media. The culture was incubated at 37° C., 200 rpm for 24 hrs. Then, the fungal biomass was collected through Miracloth and washed with sterilized water. The fungal biomass culture was then mixed with 50 ml of sterilized water and transferred 5 ml to 50 ml of three different carbon source media; 1) Promosoy special media (45) with modification (13), called High Maltose Media (HMM), 2) minimal media (6 g/L of $NaNO_3$, 0.52 g/L of KCl, 0.52 g/L of $MgSO_4$ $7H_2O$, 1.52 g/L of $KH_2PO_4$, 1 ml/L trace element solution adjust with pH6.5 (21)) plus 10% of D-glucose (MM plus glucose), or 3) minimal media with 10% of xylose (MM plus xylose). The cultures were incubated at 37° C., 200 rpm for 24 hours and 48 hours for A5IL97 gene expression, and for 48 hours for biomass quantification, enzyme activity test, and total protein quantification.

i) Biomass Quantification: Fungal biomass was measured after the culture was filtered and lyophilized for 2 days.

ii) Enzyme Activity Test: The β-glucosidase enzymatic assays were performed with 1 mM of 4-nitrophenyl-β-D-glucopyranoside (pNPG; Sigma, St. Louis Mo.). The substrates were mixed with 10 ul of fungal supernatant in 100 mM MES buffer pH 6.5 and incubated for 30 min incubation at 85° C., followed by addition of an equal volume of 2% $Na_2CO_3$ to stop the reaction. The liberated 4-nitrophenyl was detected by absorbance at 410 nm (Molecular Devices, Sunnyvale Calif.).

iii) Total Protein Quantification: Total protein of the media supernatant was determined by Bradford assay (Bio-Rad, Hercules Calif.).

A5IL97 Gene Expression

Total RNA was extracted from each lyophilized fungal biomass by using Trizol method (Thermo Fisher Scientific, Waltham, Mass.). Ten micro-gram of total RNA was cleaned with DNase I, following manufactures instructions (New England Biolabs, Ipswich, Mass.) and checked the quality and quantity on Agilent RNA 6000 nano kit using 2100 Bioanalyzer (Agilent technologies. La Jolla, Calif.). One microgram of total RNA was synthesized to cDNA using iScript™ cDNA synthesis kit (Bio-Rad, Hercules, Calif.). Fifty nanogram of each cDNA was used for qRT-PCR using SsoAdvanced Universal SYBR Green Supermix in CFX96 real-time PCR machine (Bio-Rad, Hercules, Calif.). Relative A5IL97 mRNA expression was measured using A5IL97qPCRFor A5IL97qPCRRev for A5IL97 gene expression and actinqPCRFor and actinqPCRRev for actin gene expression as an endogenous control. Both gene expressions were calculated using $\Delta\Delta$Ct method and normalized to glaA promoter at 24 hours (46). The experiment was performed with three biological replications with two different total RNA.

Statistical Analysis

Statistical difference was analyzed using JMP® version 12.2.0 software package (SAS Institute Inc. Cary, N.C.). Biomass measurement, enzyme activity, total protein quantification, and A5IL97 gene expression was analyzed and compared to each promoter strain. Statistically significant mean values, indicated with different alphabet, are significant at $P<0.05$.

AtfA Expression in E. coli

To identify atfA (transcript ID #1135913, protein ID #1135637 in Aspergillus niger ATCC1015 genome sequence v.4.0, available at US DOE Joint Genome Institute) binding sites to ecm33 promoter region, cDNA of atfA was amplified from promoter ecm33 mutant with Atf1ExpressionFor and Atf1ExpressionRev primers using Pfu Ultra high-fidelity DNA polymerase (Agilent, Santa Clara, Calif.), following the manufactures instructions. The PCR fragment was integrated to pET30a+ through quick-change mutagenesis method (47) and transformed into E. coli DH5a for the cloning and BL21Star™ (DE3) for protein expression (Thermo Fisher Scientific, Waltham, Mass.). The expression clone was incubated at 37° C. in terrific broth medium containing 2% glucose with 50 ug/ml kanamycin to an $OD_{600}$ of 0.6. Then, the expression was induced by adding 0.5 mM of isopropyl-β-D-1thiogalactopyraoside (IPTG) and continuously incubated for 5 hours at 37° C. The cell culture was harvested by centrifugation at 10000 rpm at 4° C. and lysed by freeze-thawing method. The collected soluble fractions were analyzed by sodium dodecyl sulfate-polyacrylamide gel electrophoresis (SDS-PAGE), following Coomassie blue staining. Recombinant Atf1 was purified by gravity column using the HisPur™ Ni-NTA resin (Thermo Fisher Scientific, Waltham, Mass.) with Tris-HCl pH8.0 and appropriate amount of imidazole and sodium chloride.

Gel Shift Assay

Oligonucleotides, listed in Table 2 were end-labelled at the 3'end with biotin (Thermo Fisher Scientific, Waltham, Mass.) according to the manufacturer's instructions. Complementary oligonucleotides were mixed, diluted and annealed using thermal cycler, following 95° C. for 5 min by cooling 1° C. per min until 4° C. All the reaction from Lightshift® Chemiluminescent EMSA kit with the annealed oligonucleotides were mixed, following manufacturer's instructions (Thermo Fisher Scientific, Waltham, Mass.). Briefly, the reaction mixture was incubated for 20 min at room temperature while competitor DNAs were incubated with AtfA protein at room temperature for 10 min before addition of biotin-labeled oligonucleotides. The mixtures were loaded to pre-run 6% DNA retardation gels in 0.5×TBE (Tris-boric acid-EDTA) buffer at 100 V and then blotted to nitrocellulose membrane through XCell SureLock Mini-Cell Blot Module (Thermo Fisher Scientific, Waltham, Mass.) at 380 mA for 30 min. The blotted membrane was cross-linked under UV light and detected by Chemiluminescent Hybridization and Detection kit (Thermo Fisher Scientific, Waltham, Mass.).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. An *Aspergillus niger* host cell comprising a nucleic acid encoding a gene of interest operatively linked to an ecm33 promoter of an ascomycete fungi, wherein the gene of interest is heterologous to the ecm33 promoter and/or to the *Aspergillus niger* host cell.

2. The *Aspergillus niger* cell of claim 1, wherein the ascomycete fungi is an *Aspergillus* species.

3. The *Aspergillus niger* cell of claim 2, wherein the *Aspergillus* species is an *Aspergillus niger*.

4. The *Aspergillus niger* host cell of claim 3, wherein the *Aspergillus niger* is an *Aspergillus niger* strain 1015.

5. The *Aspergillus niger* host cell of claim 1, wherein the ecm33 promoter comprises the nucleotide sequence of SEQ ID NO:1.

6. The *Aspergillus niger* host cell of claim 1, wherein the gene of interest is a glycoside hydrolase enzyme.

7. The *Aspergillus niger* host cell of claim 6, wherein the glycoside hydrolase enzyme is a glucosidase.

8. The *Aspergillus niger* host cell of claim 1, wherein the ecm33 promoter is heterologous to *Aspergillus niger* host cell.

9. The *Aspergillus niger* host cell of claim 8, wherein the gene of interest is heterologous to *Aspergillus niger* host cell.

10. The *Aspergillus niger* host cell of claim 1, wherein the gene of interest is heterologous to *Aspergillus niger* host cell.

11. A method of expressing a heterologous gene of interest in an *Aspergillus niger* host cell, comprising: (a) introducing a nucleic acid encoding a queen of interest operatively linked to an ecm33 promoter of an ascomycete fungi, wherein the queen of interest is heterologous to the ecm33 promoter and/or to *Aspergillus niger*, into an *A. niger* host cell, and (b) culturing or growing the host cell in a medium for expressing the gene of interest.

12. The method of claim 11, further comprising (c) separating or purifying a gene product encoded by the gene of interest from the host cell and/or medium.

* * * * *

SEQUENCE LISTING

```
<160> NUMBER OF SEQ ID NOS: 29

<210> SEQ ID NO 1
<211> LENGTH: 1000
<212> TYPE: DNA
<213> ORGANISM: Aspergillus niger

<400> SEQUENCE: 1
attgcttgga gtccgatttc aagctgccgc atcggctcga gcatcgtaca caagcactag      60
aagcctatgc ttggtatgaa tggtcaggac ttactgaaag accgggggaa gaaagggaag     120
aaggggggag gaagaggagc cagagggcag gcagaacgaa tcagcagacg catgagcaag     180
aagttggtca ttggcgaggt gttacaggat ggagcagact aaaccaaatg gaccgaccat     240
tcgtttccag gaccaagatc aggattcctc gatttctttt tccgctctcc gttaccgtgg     300
gccaatcgcc cctcgaagtt aattaattaa acccggacag gtacatgaaa gtgagtaaat     360
tacggtacgg gcagcgttca tacgctggtc cggtaacgtc gcaaggagag aaaggcgccc     420
```

-continued

| | |
|---|---|
| ccctccccgg tctcaggtcc accagccttt tcggggccac gactcctttc ttgccttggt | 480 |
| ttgtcctccc tgaaagtctt cccactttct tctgaagaag attttctttt ccagccatcc | 540 |
| agtccttctt ttcccttttcc tctctcgttt ctctcgcttt cctctgtcct tcccttcttc | 600 |
| tttcccctttc ttcccttccc gtgcaaatcg tgcctgccta acccgcgcac tttctctcgc | 660 |
| tgagggtctt cgctcataaa gcttctcctt cgttgaagct cttctccatt cgctcgctcg | 720 |
| cttatttatt gtctcacaaa ccccccttca gctcttacgc tgctatccgt gtcaacaaag | 780 |
| ggccttgcct cgccccagtt cgcatacttg accaacagcc gtcattggta ggtcaacctc | 840 |
| ttcatcaagc tgctgtctga tctgtttatc ttttgcgcct gccacgactg ggattggatc | 900 |
| tgttggatcg gaagggcctt ggcagtgatt taggagcaga cgaagcgaac attggtgact | 960 |
| gacatctttt cgactataca gtctcaagtt atcctaagca | 1000 |

```
<210> SEQ ID NO 2
<211> LENGTH: 12
<212> TYPE: DNA
<213> ORGANISM: Aspergillus niger
<220> FEATURE:
<221> NAME/KEY: misc_feature
<222> LOCATION: (4)..(9)
<223> OTHER INFORMATION: n is a, c, g, or t

<400> SEQUENCE: 2
```

| | |
|---|---|
| cggnnnnnnc gg | 12 |

```
<210> SEQ ID NO 3
<211> LENGTH: 22
<212> TYPE: DNA
<213> ORGANISM: Aspergillus fumigatus

<400> SEQUENCE: 3
```

| | |
|---|---|
| ccgattcctc catttccaca gc | 22 |

```
<210> SEQ ID NO 4
<211> LENGTH: 21
<212> TYPE: DNA
<213> ORGANISM: Aspergillus fumigatus

<400> SEQUENCE: 4
```

| | |
|---|---|
| cattcagaga gctacccgta g | 21 |

```
<210> SEQ ID NO 5
<211> LENGTH: 51
<212> TYPE: DNA
<213> ORGANISM: Aspergillus fumigatus

<400> SEQUENCE: 5
```

| | |
|---|---|
| ctccttcaat atcatcttct gtcagtagaa tgttgtggaa tcgtttaaag c | 51 |

```
<210> SEQ ID NO 6
<211> LENGTH: 11
<212> TYPE: DNA
<213> ORGANISM: Aspergillus fumigatus

<400> SEQUENCE: 6
```

| | |
|---|---|
| attcgctagt g | 11 |

```
<210> SEQ ID NO 7
<211> LENGTH: 21
<212> TYPE: DNA
<213> ORGANISM: Aspergillus fumigatus
```

```
<400> SEQUENCE: 7
gcagagatat ttgagggcac c                                              21

<210> SEQ ID NO 8
<211> LENGTH: 23
<212> TYPE: DNA
<213> ORGANISM: Aspergillus fumigatus

<400> SEQUENCE: 8
cttacgatgc aagatgaata cga                                            23

<210> SEQ ID NO 9
<211> LENGTH: 23
<212> TYPE: DNA
<213> ORGANISM: Aspergillus fumigatus

<400> SEQUENCE: 9
gacagaagat gatattgaag gag                                            23

<210> SEQ ID NO 10
<211> LENGTH: 23
<212> TYPE: DNA
<213> ORGANISM: Aspergillus fumigatus

<400> SEQUENCE: 10
gatttcagta acgttaagtg gat                                            23

<210> SEQ ID NO 11
<211> LENGTH: 21
<212> TYPE: DNA
<213> ORGANISM: Aspergillus fumigatus

<400> SEQUENCE: 11
gtcgatgtgt gtcttgatga c                                              21

<210> SEQ ID NO 12
<211> LENGTH: 22
<212> TYPE: DNA
<213> ORGANISM: Aspergillus niger

<400> SEQUENCE: 12
gcgtttgttc atcataaccg ac                                             22

<210> SEQ ID NO 13
<211> LENGTH: 21
<212> TYPE: DNA
<213> ORGANISM: Aspergillus niger

<400> SEQUENCE: 13
gggtatttga gaggctcgta c                                              21

<210> SEQ ID NO 14
<211> LENGTH: 21
<212> TYPE: DNA
<213> ORGANISM: Artificial Sequence
<220> FEATURE:
<223> OTHER INFORMATION: Primer for PCR amplification

<400> SEQUENCE: 14
ggtaccctac caatgctctc g                                              21

<210> SEQ ID NO 15
```

<211> LENGTH: 21
<212> TYPE: DNA
<213> ORGANISM: Artificial Sequence
<220> FEATURE:
<223> OTHER INFORMATION: Primer for PCR amplification

<400> SEQUENCE: 15
gaagagcatg gctcctcatc c                                              21

<210> SEQ ID NO 16
<211> LENGTH: 26
<212> TYPE: DNA
<213> ORGANISM: Aspergillus niger

<400> SEQUENCE: 16
gtcagtcacc gtcgcggtcg acgttc                                         26

<210> SEQ ID NO 17
<211> LENGTH: 21
<212> TYPE: DNA
<213> ORGANISM: Aspergillus niger

<400> SEQUENCE: 17
gccatcctga ataacatcgg g                                              21

<210> SEQ ID NO 18
<211> LENGTH: 22
<212> TYPE: DNA
<213> ORGANISM: Aspergillus niger

<400> SEQUENCE: 18
tcggttcatg caccagttta ac                                             22

<210> SEQ ID NO 19
<211> LENGTH: 21
<212> TYPE: DNA
<213> ORGANISM: Aspergillus niger

<400> SEQUENCE: 19
cgaacttgac gagatgacca c                                              21

<210> SEQ ID NO 20
<211> LENGTH: 21
<212> TYPE: DNA
<213> ORGANISM: Aspergillus niger

<400> SEQUENCE: 20
cgtaaggatc tgtacggcaa c                                              21

<210> SEQ ID NO 21
<211> LENGTH: 21
<212> TYPE: DNA
<213> ORGANISM: Aspergillus niger

<400> SEQUENCE: 21
cttggagatc cacatctgct g                                              21

<210> SEQ ID NO 22
<211> LENGTH: 51
<212> TYPE: DNA
<213> ORGANISM: Aspergillus niger

<400> SEQUENCE: 22
cacaagtttg taaggagaag caggctatgt ctgcggctgt tacttcgacc g              51

<210> SEQ ID NO 23
<211> LENGTH: 26
<212> TYPE: DNA
<213> ORGANISM: Aspergillus niger

<400> SEQUENCE: 23
caccactttg tacaagaaag ctggtc                                    26

<210> SEQ ID NO 24
<211> LENGTH: 47
<212> TYPE: DNA
<213> ORGANISM: Artificial Sequence
<220> FEATURE:
<223> OTHER INFORMATION: Primer for PCR amplification

<400> SEQUENCE: 24
ccgtcgtagc ccctgagcag ggatagtcag gacttactga aagaccg             47

<210> SEQ ID NO 25
<211> LENGTH: 22
<212> TYPE: DNA
<213> ORGANISM: Artificial Sequence
<220> FEATURE:
<223> OTHER INFORMATION: Primer for PCR amplification

<400> SEQUENCE: 25
cggtctttca gtaagtcctg ac                                        22

<210> SEQ ID NO 26
<211> LENGTH: 23
<212> TYPE: DNA
<213> ORGANISM: Artificial Sequence
<220> FEATURE:
<223> OTHER INFORMATION: Primer for PCR amplification

<400> SEQUENCE: 26
gtcaggactt acagtaaaga ccg                                       23

<210> SEQ ID NO 27
<211> LENGTH: 23
<212> TYPE: DNA
<213> ORGANISM: Artificial Sequence
<220> FEATURE:
<223> OTHER INFORMATION: Primer for PCR amplification

<400> SEQUENCE: 27
cggtctttac tgtaagtcct gac                                       23

<210> SEQ ID NO 28
<211> LENGTH: 22
<212> TYPE: DNA
<213> ORGANISM: Artificial Sequence
<220> FEATURE:
<223> OTHER INFORMATION: Primer for PCR amplification

<400> SEQUENCE: 28
gtcaggaccc gcgcgcagac cg                                        22

<210> SEQ ID NO 29
<211> LENGTH: 22
<212> TYPE: DNA
<213> ORGANISM: Artificial Sequence
<220> FEATURE:
<223> OTHER INFORMATION: Primer for PCR amplification

```
<400> SEQUENCE: 29
cggtgtgcgc gcgggtcctg ac                                              22
```